United States Patent [19]
Lima et al.

[11] Patent Number: 5,582,972
[45] Date of Patent: Dec. 10, 1996

[54] ANTISENSE OLIGONUCLEOTIDES TO THE RAS GENE

[75] Inventors: Walter Lima, San Diego; Brett Monia, Carlsbad; Susan Freier, San Diego; David Ecker, Leucadia, all of Calif.

[73] Assignee: Isis Pharmaceuticals, Inc., Carlsbad, Calif.

[21] Appl. No.: 990,303

[22] Filed: Dec. 14, 1992

Related U.S. Application Data

[63] Continuation-in-part of Ser. No. 715,196, Jun. 14, 1991, abandoned.
[51] Int. Cl.$^6$ ............................ C12Q 1/68; C12N 15/10
[52] U.S. Cl. ..................... 435/6; 435/91.3; 435/172.1; 536/23.1; 536/24.1; 536/24.5
[58] Field of Search .............................. 536/23.1, 24.1, 536/24.5; 435/91.3, 6, 172.3, 172.1; 514/44

[56] References Cited

U.S. PATENT DOCUMENTS 5,034,506  7/1991  Summerton .......................... 528/391

OTHER PUBLICATIONS

Ausubel et al., *Current protocols in molecular biology* 1989, John Wiley, New York.
Bacon, T. A. & Wickstrom, E., Walking Along Human c-myc mRNA with Antisense Oligonucleotides: Maximum Efficacy at the 5' Cap Region, *Oncogene Res.* 1991, 6, 13.
Bhattacharyya, A. et al., RNA Bulges and the Helical Periodicity of Double-Stranded RNA, *Nature* 1990, 343, 484.
Chow, S. A. et al., RecA Protein-promoted Homologous Pairing and Strand Exchange Between Intact and Partially Single-Stranded Duplex DNA, *J. Mol. Biol.* 223 1992, 79.
Chiang, M. Y. et al., Antisense Oligonucleotides Inhibit Intercellualr Adhesion Molecule 1 Expression by Two Distinct Mechanisms, *J. Biol. Chem.* 266 1991, 18162.
Fedor, M. J. & Uhlenbeck, O. C., Substrate Sequence Effects on "Hammerhead" RNA Catalytic Efficiency, *Proc. Natl. Acad. Sci. USA* 87 1990, 1668.
Freier, S. M. & Tinoco, I. Jr., The Binding of Complementary Oligoribonucleotides to Yeast Initiator Transfer RNA, *Biochemistry* 14 1975 3310.
Freier, S. M. et al., Contributions of Dangling End Stacking and Terminal Base Pair Formation to the Stabilities of XGGCCp, XCCGGp, XGGCCyp, and XCCGGYp Helixes, *Biochemistry* 1985, 24, 4533.
Fried, M. & Crothers, D. M. Equilibria and Kinetics of lac Repressor-Operator Interactions by Polyacrylamide Gel Electrophoresis, *Nucl. Acids Res.* 1981 9, 6505.
Garner, M. M. & Revzin, A., A Gel Electrophoresis for Quantifyng the Binding of Proteins to Specific DNA Regions: Application to Components of the *Escherichia Coli* Operon Regulatory System, *Nucl. Acids Res.* 1981, 9, 3047.
Gutell, R. R. et al., Comparative Anatomy of 16-S-lie Ribosomal RNA, *Prog. Nucleic Acids Res. and Mol. Biol.* 1985, 32, 155.
Herschlag, D. & Cech, T. R., Catalysis of RNA Cleavage by the *Tetrahymena Thermophila* Ribozyme, *Biochemistry* 29 1990a, 10159.
Herschlag, D. & Cech, T. R., Catalysis of RNA Cleavage by the *Tetrahymena Thermophila* Ribozyme, *Biochemistry* 29 1990b, 10172.
Jaeger, J. A. et al., Improved Predictions of Secondary Structures for RNA, *Proc. Natl. Acad. Sci. USA* 1989, 86, 7706.
Jinno, Y. et al., A Novel Effect of EGF on mRNA Stability, *Nucl. Acids Res.* 16 1988, 4957.
P. E. Nielsen, M. et al., Sequence-Seelctive Recognition of DNA by Strand Displacement with a Thymine-Substituted Polyamide, *Science* 1991, 254, 1497.
Pyle, A. M. et al., Direct Measurement of Oligonucleotide Substrate Binding to Wild-Type and Mutant Ribozymes from *Tetrahymena*, *Proc. Natl. Acad. Sci. USA* 1990, 87, 8187.
Pontius, B. W. & Berg, P., Rapid Renaturation of Complementary DNA Strands Mediated by Cationic Detergents: A Role for High-Probability Binding Domains in Enhancing the Kinetics of Molecular Assembly Processes, *Proc. Natl. Acad. Sci. USA* 1991, 88, 8237.
Reddy, E. P., Nucleotide Sequence Analysis of the T24 Human Bladder Carcinoma Oncogene, *Science* 1983, 220, 1061.
Revzin, A., Gel Electrophoresis Assays for DNA–Protein Interactions, *Biotechniques* 1989, 7, 346.
Sambrook et al., *Molecular Cloning. A Laboratory Manual*, Second Edition 1989, Cold Spring Harbor Laboratory Press, Cold Spring Harbor.
Uhlenbeck, O. C., Complementary Oligonucleotide Binding to Transfer RNA, *J. Mol. Biol.* 65 1972, 25.
Wickstrom, E. et al., Complementary Oligonucleotide Probe of Vesicular Stomatitis Virus Matrix Protein mRNA Translation, *Biophys. J.* 49 1986, 15.
Wu, T. & Ogilvie, K. K., A Study on the Alkylsilyl Groups in Oligoribonucleotide Synthesis, *J. Org. Chem.* 55 1990, 4717.

(List continued on next page.)

*Primary Examiner*—John L. LeGuyader
*Attorney, Agent, or Firm*—Law Offices of Jane Massey Licata

[57] ABSTRACT

Methods are provided for preparing antisense oligonucleotides which take advantage of RNA secondary and tertiary structure and for preparing antisense oligonucleotides which specifically hybridize to regions of RNA secondary and tertiary structure by comparing the affinity of the oligonucleotide for a structured RNA target to the affinity of the oligonucleotide for a length-matched oligonucleotide complement, and selecting an oligonucleotide having an affinity for the structured target which is not less than one thousandth of its affinity for the length-matched oligonucleotide complement. Oligonucleotides are also disclosed which are specifically hybridizable with regions of H-ras RNA having secondary and tertiary structure.

5 Claims, 7 Drawing Sheets

OTHER PUBLICATIONS

Wu, T. et al., Preventiton of Chain Cleavage in the Chemical Synthesis of 2'-silylated oligoribonucleotides, *Nucleic Acids Res.* 17 1989, 3501.

Yoon, K. et al., The Kinetics of Codon–Anticodon Interaction in Yeast Phenylalanine Transfer RNA, *J. Mol. Biol.* 1975, 99, 507.

Fedor et al. (1990) PNAS, USA 87, 1668–1672.

Uhlmann et al. (1990) Chemical Review vol. 90(4):544–579.

Lima et al. (1992) Biochemistry vol. 31:12055–12061.

Monia et al. (1992) J. Biol. Chem. vol. 267(28):19954–19962.

Daoka et al. (1990) Oncogene Research vol. 5: 267–275.

ANTISENSE OLIGONUCLEOTIDES TO THE RAS GENE

This is a continuation-in-part application of application Ser. No. 07/715,196, filed Jun. 14, 1991, now abandoned.

FIELD OF THE INVENTION

This invention relates to a method for preparing antisense oligonucleotides which specifically hybridize to regions of RNA secondary and tertiary structure by comparing the relative affinity of the oligonucleotide for a structured RNA target to the relative affinity of the oligonucleotide for a length-matched oligonucleotide complement, and selecting an oligonucleotide with an affinity for the structured target which is not less than one thousandth of its affinity for the length-matched oligonucleotide complement. This invention also relates to oligonucleotides which are specifically hybridizable with regions of ras RNA having secondary and tertiary structure. The ras gene is a naturally occurring gene which occasionally converts to an activated form, whose expression which has been implicated in tumor formation.

BACKGROUND OF THE INVENTION

Antisense oligonucleotides are small oligonucleotides which are complementary to the "sense" or coding strand of a given gene, and as a result are also complementary to, and thus able to specifically hybridize with, the mRNA transcript of the gene. For an antisense oligonucleotide to be effective, the complementary target sequence must be available for hybridization. However, the RNA target is not a single stranded random coil but contains secondary and tertiary structures. Target RNA structure has been shown to affect affinity and rates of oligonucleotide hybridization (Freier, S. M. & Tinoco, I. Jr., *Biochemistry* 14 1975 3310. Uhlenbeck, O. C., *J. Mol. Biol.* 65 1972, 25. Yoon, K., Turner, D. H., & Tinoco, I. Jr., *J. Mol. Biol.* 99 1975, 507. Fedor, M. J. & Uhlenbeck, O. C., *Proc. Natl. Acad. Sci. USA* 87 1990, 1668. Herschlag, D. & Cech, T. R., *Biochemistry* 29 1990a, 10159. Herschlag, D. & Cech, T. R., *Biochemistry* 29 1990b, 10172) as well as efficacy of antisense oligonucleotides (Bacon, T. A. & Wickstrom, E., *Oncogene Res.* 6 1991, 13. Wickstrom, E., Simonet, W. S., Medlock, K., & Ruiz-Robles, I., *Biophys. J.* 49 1986, 15. Chiang, M. -Y., Chan, H., Zounes, M. A., Freier, S. M., Lima, W. F., & Bennett, C. F., *J. Biol. Chem.* 266 1991, 18162). However, there is a need for a method for preparing antisense oligonucleotides which takes advantage of target secondary and tertiary structure in the preparation of effective oligonucleotides.

OBJECTS OF THE INVENTION

It is an object of the invention to provide methods for preparing antisense oligonucleotides which hybridize to regions of RNA secondary and tertiary structure.

It is another object of the invention to provide oligonucleotides which are specifically hybridizable with regions of secondary and tertiary structure of a mammalian ras RNA.

SUMMARY OF THE INVENTION

In accordance with the present invention, a method is provided for preparing antisense oligonucleotides which hybridize to regions of RNA secondary and tertiary structure by comparing the relative affinity of the oligonucleotide for a structured RNA target to the relative affinity of the oligonucleotide for a length-matched oligonucleotide complement, and selecting an oligonucleotide having an affinity for the structured target which is not less than one thousandth of its affinity for the length-matched oligonucleotide complement.

Also in accordance with the present invention, oligonucleotides are provided that are specifically hybridizable with regions of secondary and tertiary structure of a human ras RNA. The oligonucleotides comprise nucleotide units sufficient in identity and number to effect such specific hybridization. It is preferred that the oligonucleotides hybridize with a hairpin structure of a human ras mRNA transcript. In a more preferred embodiment, oligonucleotides are provided which have an affinity, measured by a dissociation constant, for a ras transcript hairpin structure which is not less than one thousandth of their affinity for a length-matched oligonucleotide complement. Oligonucleotides having nearly equal affinity, i.e., not less than one tenth, for the hairpin transcript compared to a length-matched oligonucleotide complement are most preferred.

BRIEF DESCRIPTION OF THE DRAWINGS

FIG. 1 shows enzymatic structure maps of the 47-mer H-ras mRNA transcript with and without bound antisense oligonucleotides.

DETAILED DESCRIPTION OF THE INVENTION

Figure 1A:
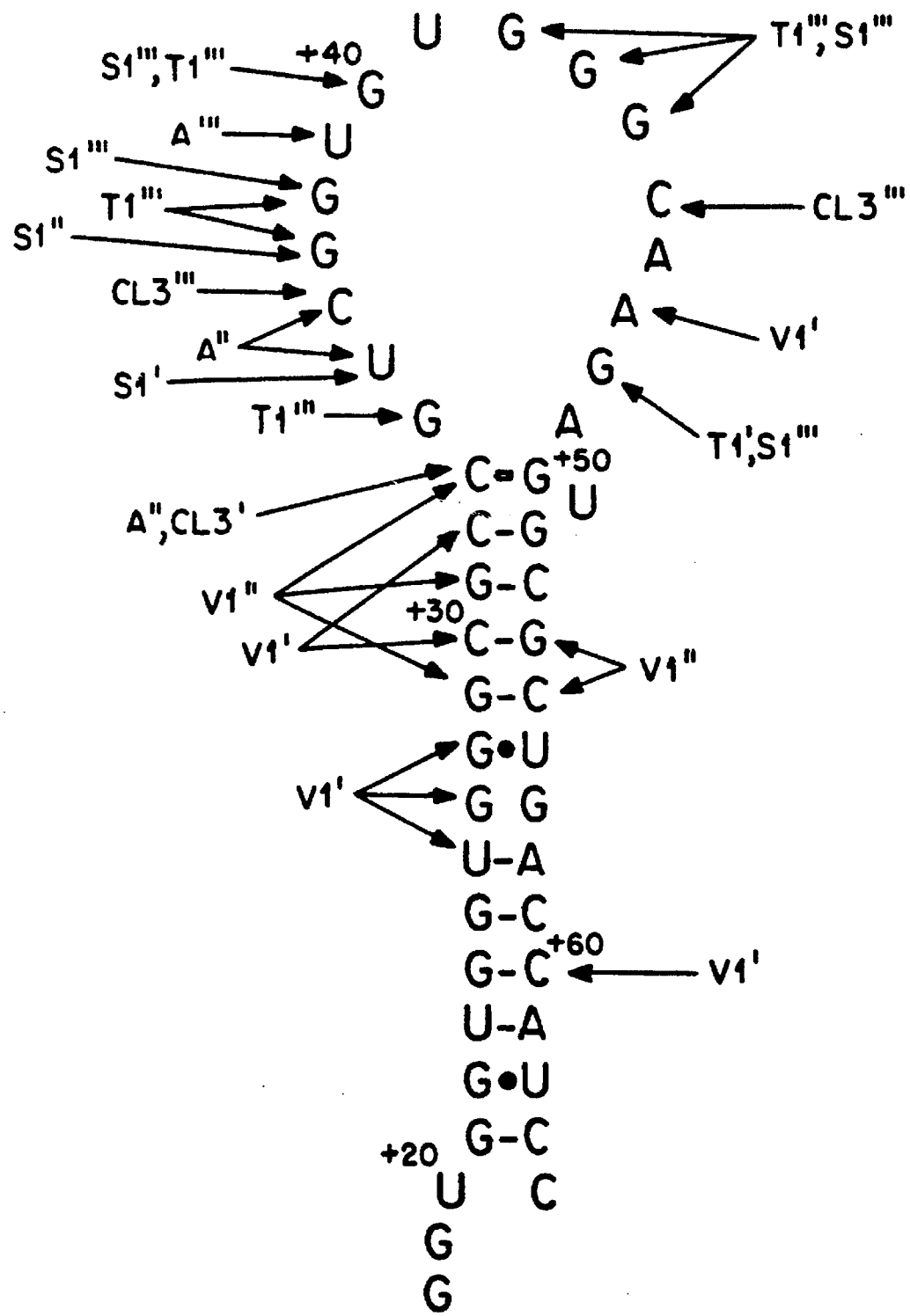
FIG. 1a is a diagram of the enzymatic structure map of the 47-mer transcript corresponding to residues 18–64 of mutant H-ras mRNA, without bound oligonucleotide (SEQ ID NO:1).

Hairpins are the predominant structure among RNA's whose secondary structure has been characterized (Gutell, R. R., Weiser, B., Woese, C. R., & Noller, H. F., *Prog.*

*Nucleic Acids Res. and Mol. Biol.* 32 1985, 155) and are frequently associated with antisense oligonucleotide target sites. To determine the effect of hairpin structure on hybridization of antisense oligonucleotides, an RNA transcript corresponding to residues +18 to +64 of activated H-ras mRNA (Reddy, E. P., *Science* 220 1983, 1061) was prepared. This target was chosen for two reasons. First, RNA folding algorithms (Jaeger, J. A., Turner, D. H., & Zuker, M., *Proc. Natl. Acad. Sci. USA* 86 1989, 7706) predict this region to be folded into a stable hairpin structure. Mapping data were used to confirm this prediction. Second, this fragment contains codon 12, the site of a point mutation believed to be responsible for the transforming activity of mutant H-ras (Reddy, E. P., *Science* 220 1983, 1061). The affinity of antisense oligonucleotides for this target site was evaluated.

Six antisense decaribonucleotides (10-mers) complementary to various regions of the ras mRNA hairpin were synthesized. Two are complementary to the stem region of this hairpin, one is partially complementary to the stem and partially complementary to the loop, and the remainder target various regions of the loop. Equilibrium and rate constants were determined for hybridization of the 10-mers to the hairpin. Comparison of affinities and rates for hybridization to the hairpin with hybridization to length-matched single stranded oligoribonucleotide complement shows that loop structure has a very large effect on hybridization of antisense oligonucleotides. The three antisense oligonucleotides targeted to the stem region of the hairpin exhibited $10^5$ to $10^6$ fold lower affinity for the hairpin target than for the length-matched target. This difference is believed to be because base pairs in the stem must be disrupted before the antisense oligonucleotide can bind.

In contrast, no significant secondary structure need be disrupted in the single stranded target. It was surprisingly found, however, that affinity for the hairpin structure of the three oligonucleotides targeted to the loop depends on the target site within the loop region. The affinity for binding to one region of the loop was found to be similar to that of binding to a stem region. The affinity for binding to another region of the loop, on the other hand, was found to be slightly better than for binding to the free single strand length-matched oligonucleotide complement. This phenomenon cannot be explained by simple base pairing thermodynamics. Because loop structure affects hybridization affinities, preparation of effective antisense oligonucleotides requires consideration of target tertiary as well as secondary structure. Affinity of an antisense oligonucleotide for the RNA target can be directly compared to affinity of the antisense oligonucleotide for a length-matched oligonucleotide complement. This can be done quantitatively by measuring the dissociation constant of the oligonucleotide hybridizing to the RNA target and the dissociation constant of the same antisense oligonucleotide hybridizing to the length-matched oligonucleotide complement. From each dissociation constant, its reciprocal, the association constant, is calculated. The ratio of the two association constants provides a parameter for use in the preparation of antisense oligonucleotides which take into consideration the effects of target structure.

Association constants for hybridization of antisense oligonucleotides to the RNA hairpin. Table 1 describes the six decaribonucleotides for which dissociation constants were measured. Two, 3270 (SEQ ID NO:2) and 3271 (SEQ ID NO:3), are complementary to the stem region of this hairpin; one, 3292 (SEQ ID NO:4), is partially complementary to the stem and partially complementary to the loop; the others target the 5' side [3291 (SEQ ID NO:5)], the middle [3283 (SEQ ID NO:6)] and the 3' side [3284 (SEQ ID NO:7)] of the loop.

TABLE 1

Antisense oligonucleotides targeted to ras hairpin
(oligonucleotides shown 5' to 3')

| Oligonucleotide | Sequence | SEQ ID NO: |
|---|---|---|
| ISIS 3270 | CACCACCACC | 2 |
| ISIS 3271 | GCGCCCACCA | 3 |
| ISIS 3292 | CGACGGCGCC | 4 |
| ISIS 3291 | CACACCGACG | 5 |
| ISIS 3283 | UUGCCCACAC | 6 |
| ISIS 3284 | CACUCUUGCC | 7 |

For each antisense oligonucleotide, dissociation constants were measured using the gel shift assay. FIG. 3 plots percent target shifted as a function of antisense concentration for each antisense oligonucleotide and each of two targets, the 47-mer hairpin and a complementary single stranded RNA 10-mer. For each dissociation constant, its reciprocal, the association constant ($K_a$), was determined. Association constants determined from these curves are listed in Table 2.

TABLE 2

Association constants for six antisense oligonucleotides hybridizing to a 47-mer hairpin target and single stranded complementary 10-mer targets

|  | Oligonucleotide | Complementary residues in hairpin target | $K_a$ hairpin target ($M^{-1}$) | $K_a$ single stranded oligonucleotide target ($M^{-1}$) | ratio[b] |
|---|---|---|---|---|---|
|  | 3270 | 18–27 | $1 \times 10^5$ | $3 \times 10^{10}$ | $3 \times 10^{-6}$ |
| stem { | | | | | |
|  | 3271 | 23–32 | $1 \times 10^6$ | $1 \times 10^{11}$ | $1 \times 10^{-5}$ |
|  | 3292 | 28–37 | $2 \times 10^5$ | $5 \times 10^{10}$ | $4 \times 10^{-6}$ |
|  | 3291 | 33–42 | $\geq 3 \times 10^{10}$ | $2 \times 10^{10}$ | $\geq 1.5$ |
| loop { | 3283 | 38–47 | $2 \times 10^9$ | $2 \times 10^{10}$ | $1 \times 10^{-1}$ |
|  | 3284 | 43–52 | $<1 \times 10^5$ | $2 \times 10^{10}$ | $<5 \times 10^{-6}$ |

[a]Hybridization conditions are given in the text. Estimated errors are ± a factor of two.
[b]Ratio of $K_a$ for the 47-mer hairpin target to $K_a$ for a single stranded 10-mer target.

The three antisense oligonucleotides targeted to the stem region of the hairpin exhibited $10^5$ to $10^6$ fold lower affinity for the hairpin target than for the length-matched target. For the three oligonucleotides targeted to the loop, the thermodynamic effect of the hairpin depends on the target site. Oligonucleotide 3284 (SEQ ID NO:7), targeted to the 3' side of the loop, binds with nearly a millionfold lower affinity to the hairpin than to its complementary 10-mer. Oligonucleotide 3283 (SEQ ID NO:6), targeted to the middle of the loop, binds with tenfold lower affinity to the hairpin than to the complementary 10-mer, but oligonucleotide 3291 (SEQ ID NO:5), targeted to the 5' side of the loop, binds at least as well to the hairpin as to its 10-mer complement.

Structured single stranded regions impact antisense binding: The effect of target secondary structure on antisense oligonucleotide binding is demonstrated by the difference between $K_a$'s for the oligonucleotide-hairpin hybrids and the oligonucleotide-oligonucleotide complexes (last column in Table 2). For oligonucleotides targeted to the stem of the hairpin, binding affinity to the hairpin is $10^5$–$10^6$ fold less than for binding to a 10-mer target. This difference is believed to be due to the need for disruption of base pairs in the stem before the antisense oligonucleotide can bind. In contrast, no significant secondary structure need be disrupted in the single stranded target. For example, thermodynamic parameters for RNA folding (Jaeger, J. A., Turner, D. H., & Zuker, M., *Proc. Natl. Acad. Sci. USA* 86 1989, 7706), predict disruption of stem residues necessary to bind 3292 (SEQ ID NO:4) requires +8.9 kcal/mol, thus predicting the antisense oligonucleotide will bind $5\times10^{-7}$-fold as well to the hairpin as to a single stranded 10-mer target. Considering differences in ionic conditions, the observed ratio of $4\times10^{-6}$ for 3292 (SEQ ID NO:4) supports this prediction.

For the three oligonucleotides targeted to the loop, thermodynamic effect of the hairpin depends on target site. These effects cannot be explained by simple base-pairing thermodynamics; rather, loop structure is responsible. For all three antisense oligonucleotides, the target site is single stranded as demonstrated by cleavage with single strand-specific nucleases, and no base pairs should have to be broken for hybridization to occur. It appears the thermodynamic cost of binding to residues 43–52 is similar to that of binding to a stem region. Binding to residues 33–42, on the other hand, has a small negative cost; it is slightly easier to bind to the loop structure than the free single strand.

Migrational retardation of hybrid: For all six decaribonucleotides, hybridization of the oligonucleotide to the hairpin target reduced mobility of the hairpin on the native polyacrylamide gel. The degree of retardation correlates inversely with the association constant for this interaction.

Retardation distances support the thermodynamic results. Migrational differences between hybrid and free transcript indicate that loop structure is responsible for the difference in binding behaviors for antisense oligonucleotides targeted to the loop. Conformational changes in the transcript due to hybrid formation contribute to migrational retardation of the hybrid. Where hybridization results in significant perturbation of target secondary structures, there is greater retardation of the hybrid band; the three oligonucleotides targeted to the stem as well as oligonucleotide 3284 (SEQ ID NO:7) show large retardation on the gel. In contrast, oligonucleotide 3291 (SEQ ID NO:5) binds best to the hairpin structure and undergoes the least retardation on the gel.

Figure 1B:
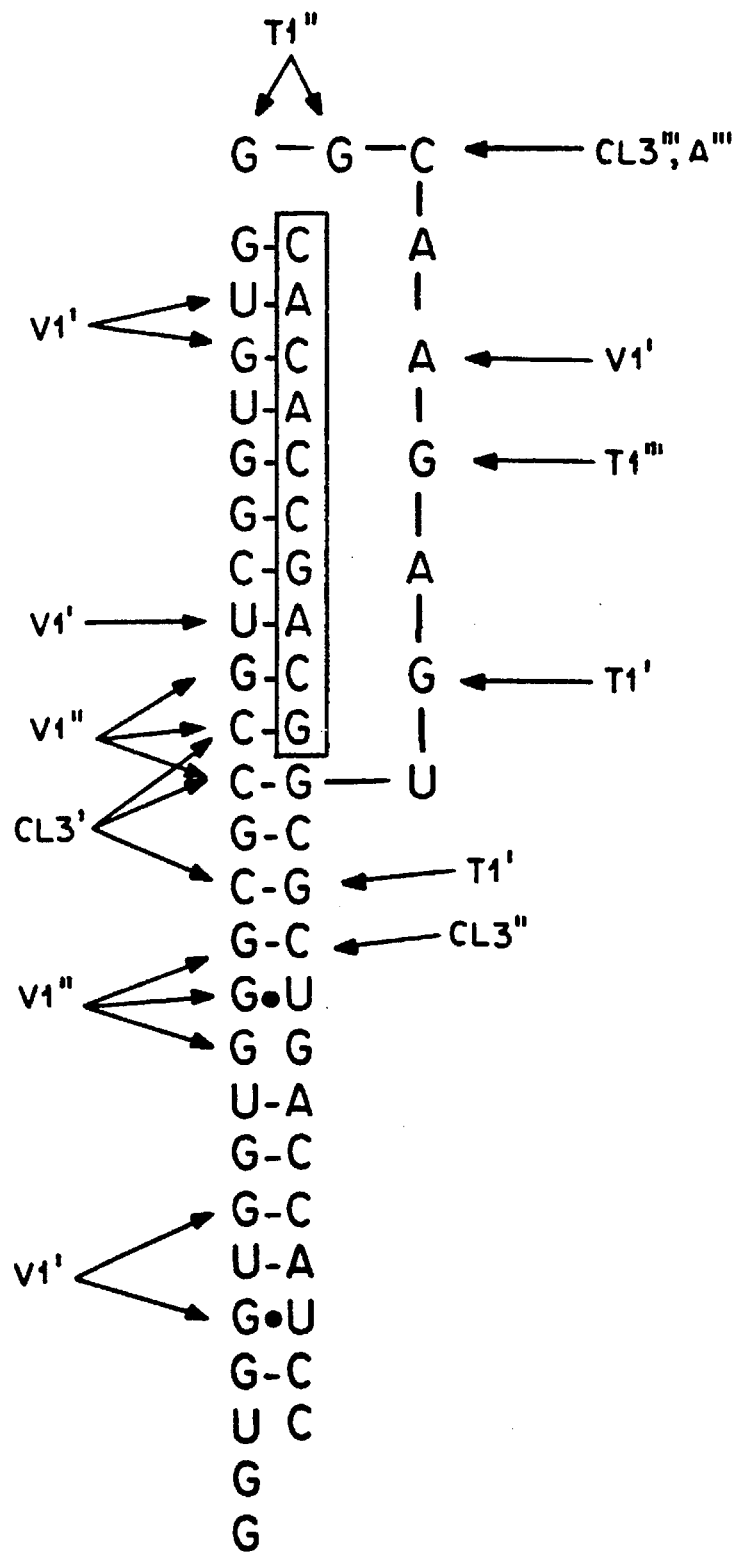
FIG. 1b is a diagram of the enzymatic structure map of the 47-mer transcript bound to oligonucleotide 3291 (SEQ ID NO:5).
Figure 1C:
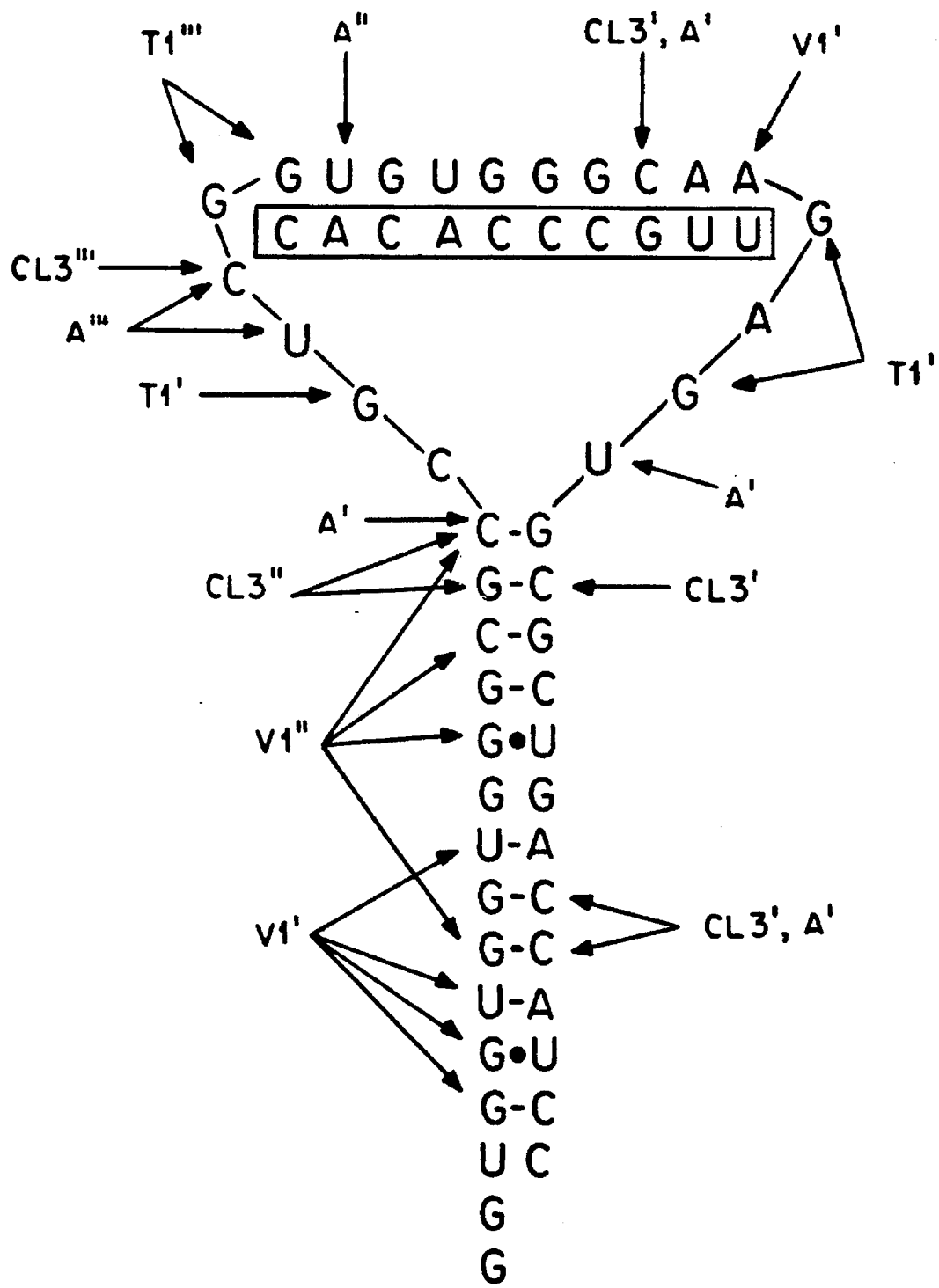
FIG. 1c is a diagram of the 47-mer transcript bound to oligonucleotide 3283 (SEQ ID NO:6). The degree of enzymatic digestion is indicated by the superscript ($^I$=weak; $^{III}$=strong). Specificity for each enzyme is as follows: RNase V1 primarily cleaves double stranded regions irrespective of sequence; RNase T1 recognizes single stranded regions and cleaves Gp↓N bonds; RNase A primarily recognizes single stranded pyrimidines and cleaves Yp↓N bonds. RNase CL3 primarily cleaves after single stranded cytidine; and RNase S1 cleaves single stranded regions indiscriminately.

Structure map of hybrid: Structure maps for oligonucleotides 3291 (SEQ ID NO:5) and 3283 (SEQ ID NO:6) bound to the ras hairpin are shown in FIGS. 1*b* and 1*c*, based on data shown in FIG. 2. In each case, upon hybridization, strong single strand-specific cleavage sites at the target site in the transcript disappear and are replaced by double strand-specific cleavage sites in the hybrid. For oligonucleotide 3291 (SEQ ID NO:5), digestion patterns for regions outside the target site are virtually identical for both the hybrid (FIG. 1*b*) and the unbound transcript (FIG. 1*a*). In contrast, for oligonucleotide 3283 (SEQ ID NO:6), digestion patterns outside the target site differ for the hybrid (FIG. 1*c*) and the unbound transcript (FIG. 1*a*). Compared to the free transcript, the hybrid shows reduced digestion with RNAse T1 at G(34) and enhanced digestion with RNAse A at U(35) and C(36). Both hybrid maps also show double strand- and single strand-specific hits at the top of the stem, indicating that this region is destabilized by formation of the hybrids.

Effects of structure on hybridization kinetics. Data in Table 3 demonstrate that thermodynamic trends noted above are due to trends in the rates of association. Whereas dissociation rates are similar for both targets and all three oligonucleotides studied, association rates vary from $10^1$ to $10^8$ $M^{-1}s^{-1}$. Oligonucleotide 3292 (SEQ ID NO:4), targeted partially to the stem and partially to the loop, binds $10^7$ times more slowly to the hairpin than to a single stranded 10-mer target. In contrast, oligonucleotide 3291 (SEQ ID NO:5), targeted to the 5' side of the loop, binds faster to the hairpin than to a single stranded target. In fact, $k_1$ for binding oligonucleotide 3291 (SEQ ID NO:5) to the hairpin is approximately 10-fold faster than association rates reported for other structured RNA hybrids (Yoon, K., Turner, D. H., & Tinoco, I. Jr., *J. Mol. Biol.* 99 1975, 507; Fedor, M. J. & Uhlenbeck, O. C., *Proc. Natl. Acad. Sci. USA* 87 1990, 1668; Chow, S. A., Chiu, S. -K., & Wong, B. C., *J. Mol. Biol.* 223 1992, 79) demonstrating that a particularly favorable loop structure is involved.

TABLE 3

Rate constants for three antisense oligonucleotides hybridizing to a 47-mer hairpin target and single stranded complementary 10-mer targets.[a]

| | | OBSERVED[b] | | CALCULATED[c] | |
|---|---|---|---|---|---|
| Oligonucleotide | | $k_1$ ($s^{-1}$) | $k_1$ ($M^{-1}s^{-1}$) | $k_1$ ($M^{-1}s^{-1}$) | ratio[d] |
| 47-mer | 3292 | $1 \times 10^{-4}$ | 13 | 19 | $10^{-7}$ |
| | 3291 | $2 \times 10^{-2}$ | — | $\geq 2 \times 10^8$ | $\geq 2.5$ |
| target | 3283 | $1 \times 10^{-2}$ | $6 \times 10^6$ | $1 \times 10^7$ | 0.25 |
| 10-mer | 3292 | $4 \times 10^{-3}$ | — | $2 \times 10^8$ | |
| | 3291 | $2 \times 10^{-2}$ | $1 \times 10^7$ | $8 \times 10^7$ | |
| target | 3283 | $2 \times 10^{-2}$ | — | $4 \times 10^7$ | |

[a]Hybridization conditions are given in the text. Antisense oligonucleotides are described in Table 1. Estimated errors are ± a factor of two.
[b]Rates were determined experimentally as described in Materials and Methods.
[c]Association rate was calculated from the measured dissociation rate and the measured equilibrium constant.
[d]Ratio of $k_1$ for the 47-mer hairpin target to $k_1$ for a single stranded 10-mer target.

The present invention employs oligonucleotides for use in antisense inhibition of the function of RNA and DNA deriving from the ras gene. In the context of this invention, the term "oligonucleotide" refers to an oligomer or polymer of ribonucleic acid or deoxyribonucleic acid. This term includes oligomers consisting of naturally occurring bases, sugars and intersugar (backbone) linkages as well as oligomers having non-naturally occurring portions which function similarly. Such modified or substituted oligonucleotides are often preferred over native forms because of properties such as, for example, enhanced cellular uptake and increased stability in the presence of nucleases.

Specific examples of some preferred oligonucleotides envisioned for this invention may contain phosphorothioates, phosphotriesters, methyl phosphonates, chain alkyl or cycloalkyl intersugar linkages or short chain heteroatomic or heterocyclic intersugar linkages. Also preferred are oligonucleotides having morpholino backbone structures. Summerton, J. E. and Weller, D. D., U.S. Pat. No. 5,034,506. In other preferred embodiments, such as the protein-nucleic acid (PNA) backbone, the phosphodiester backbone of the oligonucleotide may be replaced with a polyamide backbone, the bases being bound directly or indirectly to the aza nitrogen atoms of the polyamide backbone. P. E. Nielsen, M. Egholm, R. H. Berg, O. Buchardt, *Science* 1991, 254, 1497. Other preferred oligonucleotides may contain alkyl and halogen-substituted sugar moieties, most preferably comprising a 2'-O-alkyl or a halogen modification at the 2' position. Oligonucleotides may also have sugar mimetics such as cyclobutyls in place of the pentofuranosyl group.

The oligonucleotides in accordance with this invention preferably comprise from about 6 to about 30 nucleic acid base units. It is more preferred that such oligonucleotides comprise from about 8 to 25 nucleic acid base units, and still more preferred to have from about 9 to 20 nucleic acid base units. As will be appreciated, a nucleic acid base unit is a base-sugar combination suitably bound to adjacent nucleic acid base unit through phosphodiester or other bonds.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed, however the actual synthesis of the oligonucleotides are well within the talents of the routineer. It is also well known to use similar techniques to prepare other oligonucleotides such as the phosphorothioates and alkylated derivatives.

In accordance with this invention, persons of ordinary skill in the art will understand that messenger RNA identified by the open reading frames (ORFs) of the DNA from which they are transcribed includes not only the information from the ORFs of the DNA, but also associated ribonucleotides which form regions known to such persons as the 5'-untranslated region, the 3'-untranslated region, and intervening sequence ribonucleotides. Thus, oligonucleotides may be formulated in accordance with this invention which are targeted wholly or in part to these associated ribonucleotides as well as to the informational ribonucleotides. In preferred embodiments, the oligonucleotides are specifically hybridizable with a transcription initiation site, a translation initiation site, an intervening sequence and sequences in the 3'-untranslated region. In a more preferred embodiment, oligonucleotides are specifically hybridizable with the codon 12 region of the ras mRNA, and in a most preferred embodiment, the oligonucleotides are specifically hybridizable with the codon 12 region of activated ras mRNA.

In accordance with this invention, the affinity of an antisense oligonucleotide for a structured RNA target is compared to the affinity of the same antisense oligonucleotide for a length-matched oligonucleotide complement. In the context of this invention, the term "length-matched oligonucleotide complement" refers to an oligonucleotide which is substantially equivalent in number of nucleotides to the antisense oligonucleotide being evaluated, and which has a sequence substantially complementary to that of the antisense oligonucleotide according to the rules for Watson-Crick base pairing.

The following examples illustrate the present invention and are not intended to limit the same.

EXAMPLES

Example 1

Materials: Unlabeled dNTP[1] and NTP, ribonucleases T1 and CL3 and calf intestine alkaline phosphatase were purchased from Boehringer Mannheim (Indianapolis, Ind.). Ribonucleases A and S1 were from Gibco BRL (Gathersburg, Md.). Ribonuclease V1, RNA ligase and RNAguard were from Pharmacia LKB (Upsalia, Sweden). [γ-$^{32}$P]ATP and [$^{32}$P]pCp were from ICN Biochemicals (Irvine Calif.) and Amersham (Arlington Heights, Ill.), respectively. T4 polynucleotide kinase and T7 RNA polymerase were from Promega (Madison, Wis.). The plasmid pT24-C3, containing the c-H-ras-1 activated oncogene (codon 12, GGC GTC) was from American Type Culture Collection (Bethesda, Md.). Sep-Pak C18 cartridges were purchased from Waters (Milford, Mass.). 5'-dimethoxy-trityl 2'-tert-butyldimethylsilyl 3'-O-phosphoramidites were from American Bionetics (Hayward, Calif.); tetrabutylammoniumfluoride was from Aldrich (Milwaukee, Wis.). Protected phosphoramidites and other standard reagents for chemical synthesis of DNA were purchased from Applied Biosystems Inc (Foster City, Calif.).

Example 2

Preparation of RNA transcripts: The template for transcription was prepared from the plasmid pT24-C3 using PCR according to standard methods (Ausubel, F. M., Brent, R., Kingston, R. E., Moore, D. D., Seidman, J. G, Smith, J. A., & Struhl, K., *Current protocols in molecular biology* 1989, John Wiley, New York). The sense primer consisted of the 17-mer responsive sequence for the T7 promoter followed by a 15-mer sequence homologous to residues +18 to +32 of the activated H-ras mRNA sequence. The antisense primer was complementary to residues +50 to +64 of the mRNA sequence. After purification on a 2% agarose gel (Jinno, Y., Merlino, G. T., & Pastan, I., *Nucl. Acids Res.* 16 1988, 4957), the template was used to synthesize a 47 base segment of activated H-ras mRNA containing codon 12 (SEQ ID NO:1). Transcripts were prepared in 100L containing 40 mM trisHCl, pH 8.1, 22 mM MgCl$_2$, 5 mM DTT, 1 mM spermidine, 0.01% triton X 100, 4 mM each rNTP, 100 U RNAguard (RNAse inhibitor), 80 mg/mL PEG, 10 nM T7 RNA polymerase and roughly 1 g template. Reactions were incubated at 37° C. for 2 hours.

Example 3

Oligonucleotide synthesis: Oligoribonucleotides were synthesized using an Applied Biosystems 380B automated DNA synthesizer and 5'-dimethoxy-trityl 2'-tert-butyldimethylsilyl 3'-O-phosphoramidites (Wu, T. & Ogilvie, K. K., *J. Org. Chem.* 55 1990, 4717). Protecting groups on the exocyclic amines of A, C and G were phenoxyacetyl (Wu, T., Ogilvie, K. K., & Pon, R. T., *Nucleic Acids Res.* 17 1989, 3501). The standard DNA synthesis cycle was modified by increasing the wait step after the pulse delivery of tetrazole to 900 s. Oligonucleotides were deprotected by overnight incubation at room temperature in methanolic ammonia. After drying in vacuo, the 2'-silyl group was removed by overnight incubation at room temperature in 1M tetrabutylammoniumfluoride in tetrahydrofuran. Oligonucleotides were purified using a C18 Sep-Pak cartridge (Freier, S. M., Alkema, D., Sinclair, A., Neilson, T., & Turner, D. H., *Biochemistry* 1985, 24, 4533; Sambrook, J., Fritsch, E. F., & Maniatis, T. (1989) in *Molecular Cloning. A Laboratory Manual, Second Edition*, Cold Spring Harbor Laboratory Press, Cold Spring Harbor) followed by ethanol precipitation. Analytical denaturing polyacrylamide electrophoresis demonstrated the RNA oligonucleotides were greater than 90% full length material.

DNA oligonucleotides used for PCR primers were synthesized using an Applied Biosystems 380B automated synthesizer and standard phosphoramidite chemistry. Primers were purified by precipitation two times out of 0.5M NaCl with 2.5 volumes ethanol.

Example 4

$^{32}$P Labeling of RNA transcripts and oligoribonucleotides: RNA transcripts and oligonucleotides were 5' end labeled with $^{32}$P using [$\gamma^{32}$P]ATP, T4 polynucleotide kinase and standard procedures (Ausubel, F. M., Brent, R., Kingston, R. E., Moore, D. D., Seidman, J. G., Smith, J. A., & Struhl, K., *Current protocols in molecular biology* 1989, John Wiley, New York). RNA transcripts were 3' end labeled with $^{32}$P using [$^{32}$P]pCp, T4 RNA ligase and standard procedures (Ausubel, F. M., Brent, R., Kingston, R. E., Moore, D. D., Seidman, J. G., Smith, J. A., & Struhl, K., *Current protocols in molecular biology* 1989, John Wiley, New York). Labeled oligonucleotides were purified using a C18 Sep-Pak (Freier, S. M., Alkema, D., Sinclair, A., Neilson, T., & Turner, D. H., *Biochemistry* 1985, 24, 4533; Sambrook, J., Fritsch, E. F., & Maniatis, T. (1989) in *Molecular Cloning. A Laboratory Manual, Second Edition*, Cold Spring Harbor Laboratory Press, Cold Spring Harbor); labeled transcripts were purified by electrophoresis on a 12% denaturing polyacrylamide gel (Sambrook, J., Fritsch, E. F., & Maniatis, T., *Molecular Cloning. A Laboratory Manual, Second Edition* 1989, Cold Spring Harbor Laboratory Press, Cold Spring Harbor). Specific activities of the labeled 47-mer and 10-mers were, respectively, about 2000 cpm/fmol and about 6000 cpm/fmol.

Example 5

Enzymatic structure mapping: To determine the effect of hairpin structure on hybridization of antisense oligonucleotides, an RNA transcript corresponding to residues +18 to +64 of activated H-ras mRNA (Reddy, E. P., *Science* 1983, 220, 1061) was prepared. This target was chosen for two reasons. Firstly, RNA folding algorithms (Jaeger, J. A., Turner, D. H., & Zuker, M., *Proc. Natl. Acad. Sci. USA* 1989, 86, 7706) predict this region to be folded into a stable hairpin structure. Hairpins are the predominant structure among RNA's whose secondary structure has been characterized (Gutell, R. R., Weiser, B., Woese, C. R., & Noller, H. F., *Prog. Nucleic Acids Res. and Mol. Biol.* 1985, 32, 155) and therefore would likely be the structure most frequently associated with an antisense oligonucleotide target site. Secondly, this fragment contains codon 12, the site of a point mutation thought to be responsible for the transforming activity of mutant H-ras (Reddy, E. P., *Science* 1983, 220, 1061) and accordingly represents an attractive target for an antisense therapeutic. Therefore, we were interested in evaluating affinity of antisense oligonucleotides for this target site. Digestions with RNAse T1, V1, CL3 and A were performed in 10L containing 10 mM trisHCl, pH 7.4, 50 mM NaCl, 5 mM MgCl$_2$, 3 g tRNA and 3.5×10$^4$ cpm of $^{32}$P labeled transcript. RNAse S1 digestions were performed in 10L containing 50 mM sodium acetate, pH 5.0, 1 mM zinc acetate, 250 mM NaCl, 3 g tRNA and 3.5×10$^4$ cpm of $^{32}$P labeled transcript. To guarantee only primary hits were detected, the concentration of each enzyme was chosen such that roughly 90% of the transcript remained intact. Reactions were incubated 5 minutes at 25° C. except for reactions containing RNAse S1 which were incubated 5 minutes at 4° C. Following incubation, reactions were quenched by addition of 5L of 9M urea. Reaction products were resolved using a 12% polyacrylamide sequencing gel (Ausubel, F. M., Brent, R., Kingston, R. E., Moore, D. D., Seidman, J. G., Smith, J. A., & Struhl, K., *Current protocols in molecular biology* 1989, John Wiley, New York).

Structures of oligonucleotide bound transcripts were mapped as described above except oligonucleotide was added for a final concentration of 10M and incubated 2 hours at 37° C. prior to enzymatic digestion.

Example 6

Figure 2:
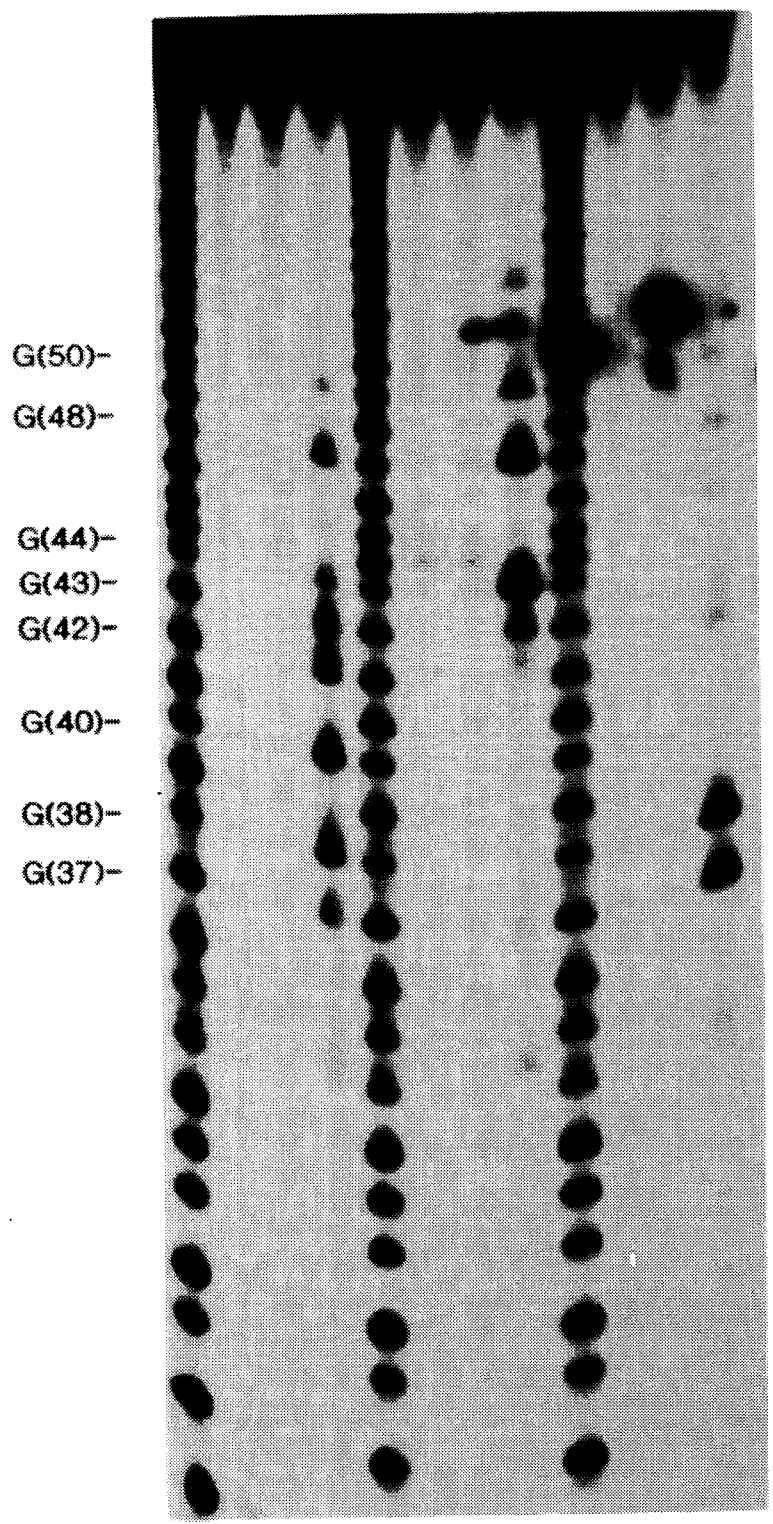
FIG. 2 is an autoradiogram of a gel showing RNAse T1 digestion of 5' end labeled 47-mer transcript with no oligonucleotide added (lanes 2–4), hybridized to oligonucleotide 3291 (SEQ ID NO:5) (lanes 6–8), or hybridized to oligonucleotide 3283 (SEQ ID NO:6) (lanes 10–12). Digestions were performed as described with 0.9 U RNAse T1 (lanes 2, 6 and 10), 1.2 U RNAse T1 (lanes 3, 7, and 11), or 1.5 U RNAse T1 (lanes 4, 8 and 12). The base hydrolysis ladder (lanes 1, 5 and 9) was prepared by incubation of 5' end labeled transcript at 90° C. for 5 m in 10L containing 100 mM sodium carbonate, pH 9.0.
Figure 3A:
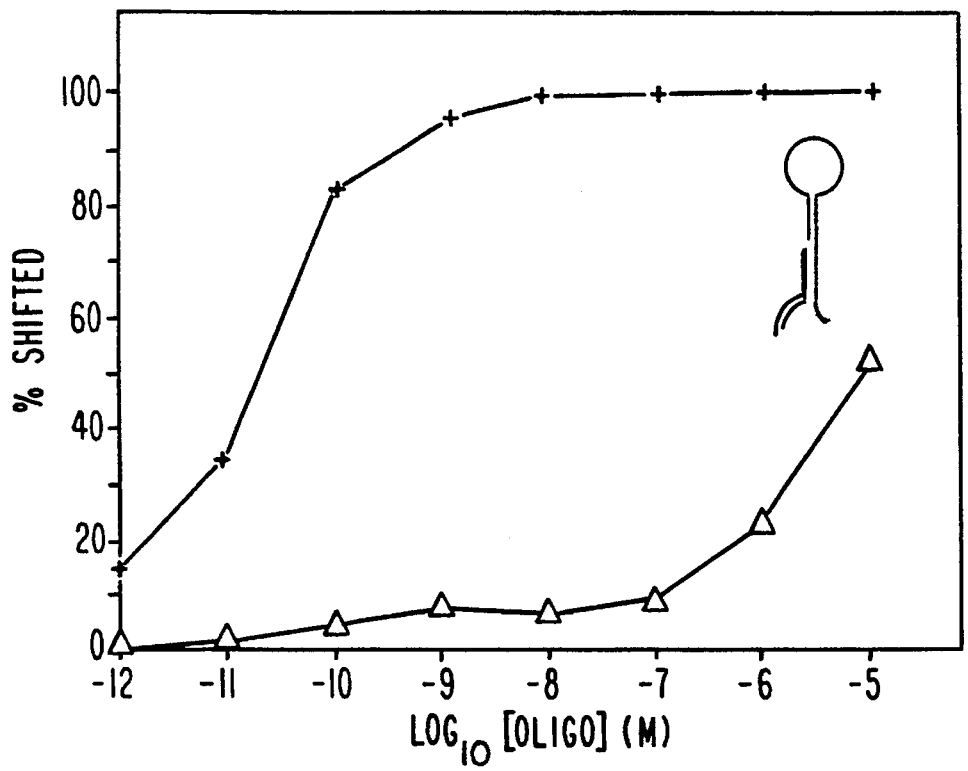
FIG. 3 is a six-panel graph showing fraction of target shifted vs concentration of antisense oligonucleotide for the six antisense oligonucleotides described in Table 1 binding to the 47-mer hairpin target (Δ) or a single stranded complementary decaribonucleotide targets (+). a) 3270 (SEQ ID NO:2); b) 3271 (SEQ ID NO:3); c) 3292 (SEQ ID NO:4); d) 3291 (SEQ ID NO:5); e) 3283 (SEQ ID NO:6); f) 3284 (SEQ ID NO:7). The double line in the schematic indicates the target site for each oligonucleotide.
Figure 3B:
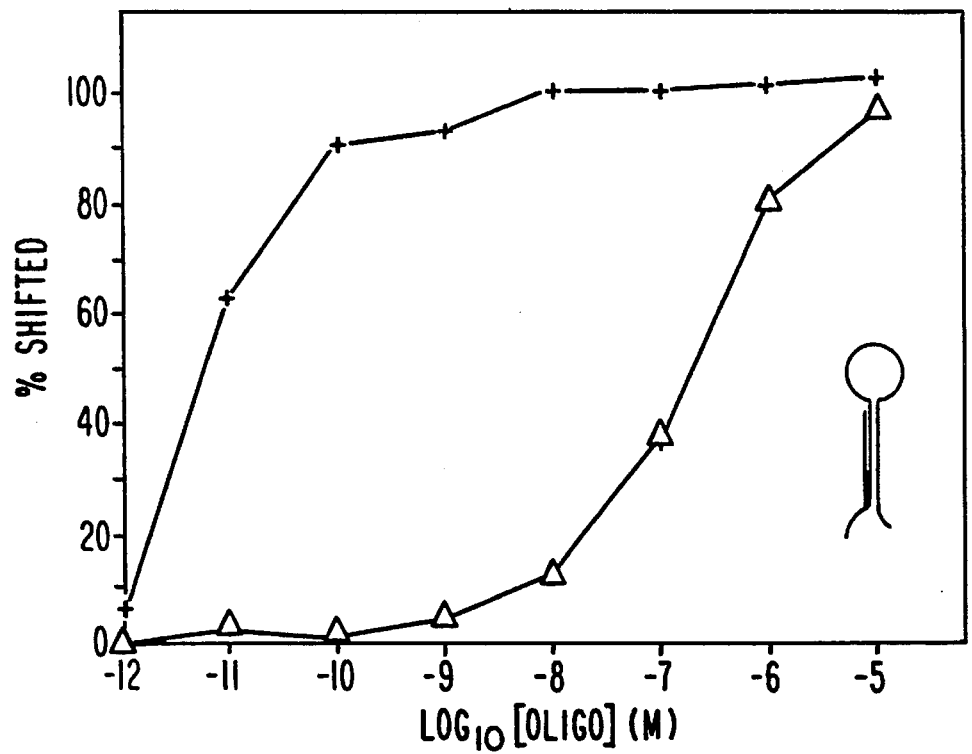
Figure 3C:
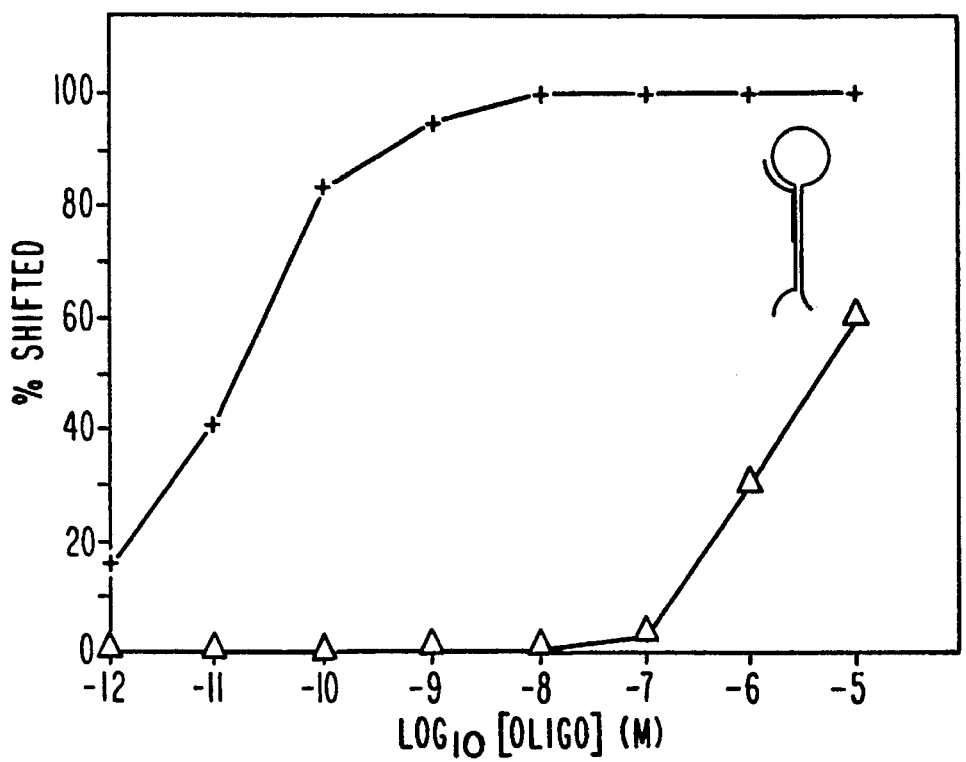
Figure 3D:
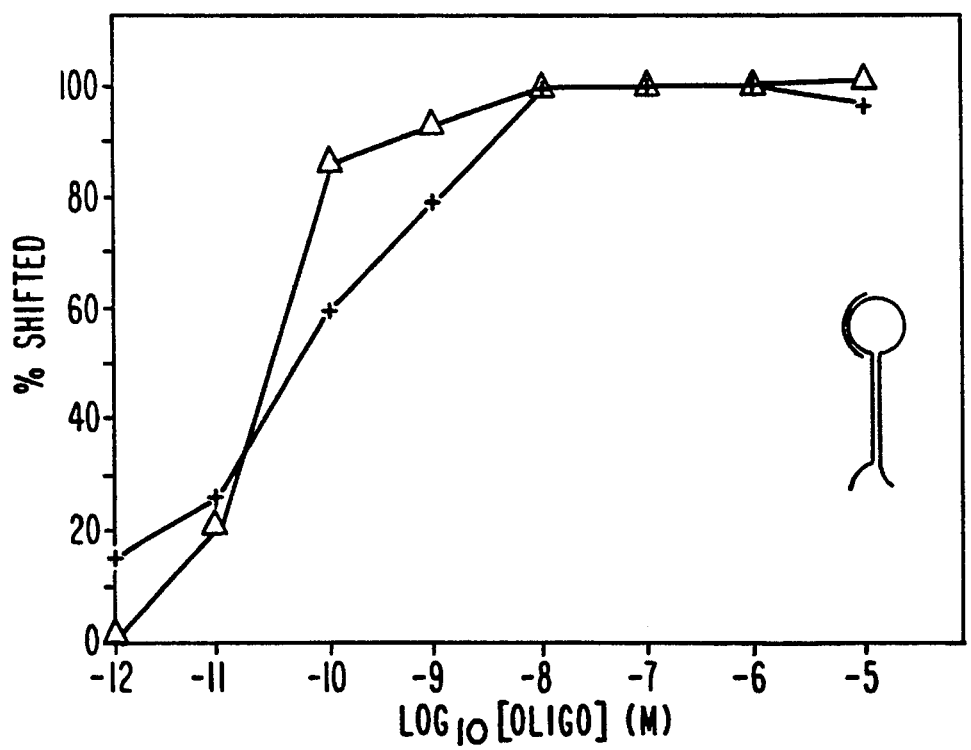
Figure 3E:
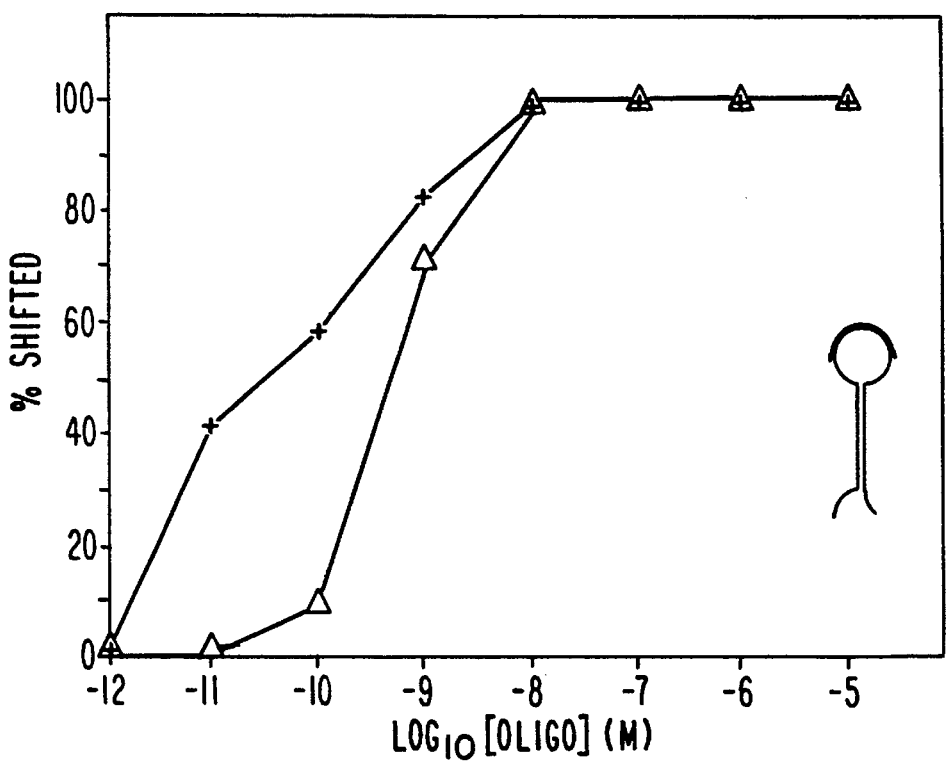
Figure 3F:
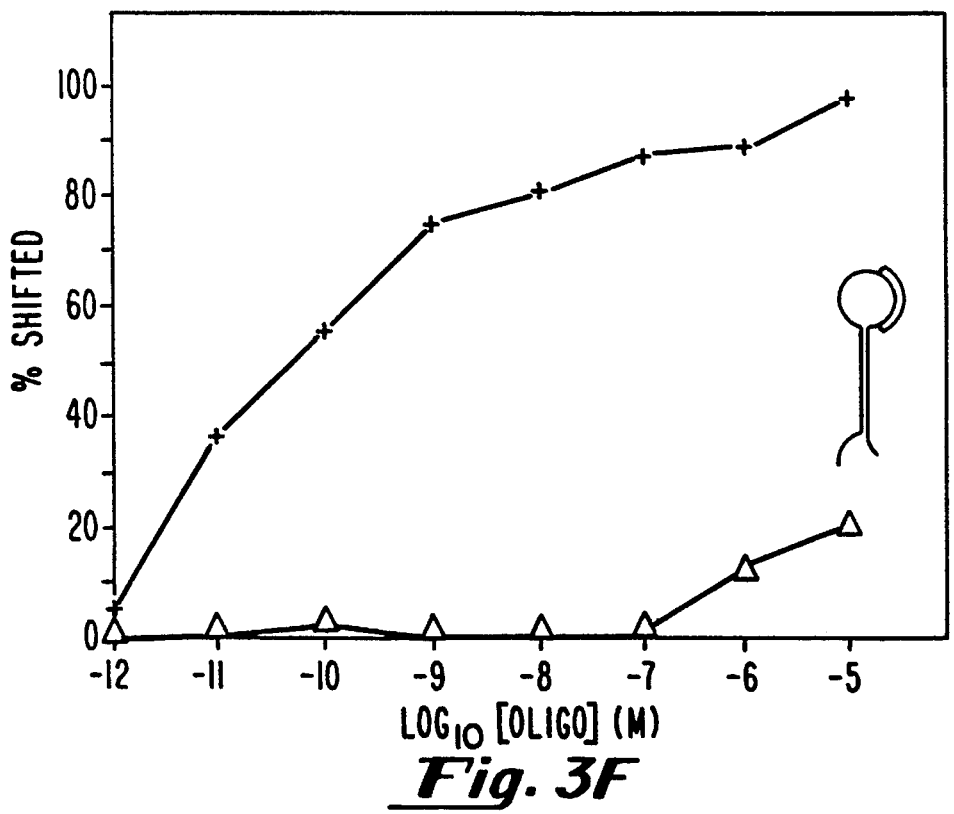

Structure map of the mRNA hairpin. The enzymatic structure map for the 47-mer transcript corresponding to residues 18–64 of mutant H-ras mRNA is shown in FIG. 1 and FIG. 2 (lanes 2–4). Enzymatic structure mapping of the 47-mer transcript reveals a hairpin structure consisting of either a 12 base pair stem and a 19 membered loop or a 13 base pair stem with a 16 membered loop. The ambiguity in the stem size is due to digestion of the C(33)–G(50) base pair with both double and single strand specific enzymes. Mapping data from both the 5' and 3' end labeled substrates demonstrate these are primary hits suggesting this base pair is transitory and both conformations are present.

Example 7

Determination of dissociation constants: Equilibrium constants for hybridization of antisense oligonucleotides to the RNA hairpin were measured using a gel shift assay (Pyle, A. M., McSwiggen, J. A., & Cech, T. R., *Proc. Natl. Acad. Sci. USA* 1990, 87, 8187; Ausubel, F. M., Brent, R., Kingston, R. E., Moore, D. D., Seidman, J. G., Smith, J. A., & Struhl, K., *Current protocols in molecular biology* 1989, John Wiley, New York; Fried, M. & Crothers, D. M., *Nucl. Acids Res.* 1981 9, 6505; Garner, M. M. & Revzin, A., *Nucl. Acids Res.* 1981, 9, 3047; Pontius, B. W. & Berg, P., *Proc. Natl. Acad. Sci. USA* 1991, 88, 8237; Revzin, A., *BioTechniques* 1989, 7, 346; Bhattacharyya, A., Murchie, A. I. H., & Lilley, D. M., *Nature* 1990, 343, 484). Hybridization reactions were prepared in 20L L containing 100 mM Na$^+$, 10 mM phosphate, pH 7.0, 1000 cpm of 5'-$^{32}$P labeled transcript and antisense oligonucleotide ranging in concentration from 1 pM to 10M and incubated 20 hours at 37° C. After addition of 10L loading buffer (15% Ficoll, 0.25% bromphenol blue, 0.25% xylene cyanole FF), reactions were resolved at 10° C. in a 12% native polyacrylamide gel containing 44 mM trisborate, 1 mM MgCl$_2$. Hybridization of antisense oligonucleotides to complementary oligonucleotide targets was measured similarly except resolution was on a native 20% polyacrylamide gel. Gels were quantitated using a Molecular Dynamics Phosphorimager. If the antisense oligonucleotide concentration significantly exceeds the target concentration, the dissociation constant ($K_d$) is simply the antisense oligonucleotide concentration at which 50% of the target is shifted. Due to the limited specific activity of the targets, concentrations were roughly 25 pM for the transcript and 8 pM for the oligonucleotide target so association constants tighter than $1.5 \times 10^{10}$ M$^{-1}$ for the 47-mer or $5 \times 10^{11}$ M$^{-1}$ for the 10-mer could not be accurately measured.

Example 8

Determination of hybridization rates: To measure bimolecular association rates ($k_1$), hybridization reactions were prepared as described above except a single antisense oligonucleotide concentration (10-fold over the $K_d$) was used. Reactions were incubated at 37° C. for prescribed intervals and quenched by snap freezing on dry ice. Reactions were individually thawed and immediately loaded onto a running native polyacrylamide gel.

To determine dissociation rates, the concentration of antisense oligonucleotide used in the $k_1$ determination was incubated with the labeled target RNA for 20 hours at 37° C. Following annealing, unlabeled target was added in 10 fold excess to the antisense oligonucleotide and reactions were incubated at 37° C. for the prescribed intervals. Reactions were snap frozen and analyzed on polyacrylamide gels as described above.

Example 9

Rate constants for hybridization of antisense oligonucleotides to the RNA hairpin: Bimolecular association rate constants ($k_1$) and dissociation rate constants ($k_{-1}$) for three oligonucleotides to each target are listed in Table 3. Association rates were calculated from the measured dissociation rate and the measured equilibrium constant, $K_a = k_1/k_{-1}$. Some association rates were also measured directly. In those cases, experimental and calculated rates correlated well.

Trends observed for $k_1$ are similar to those noted above for $K_a$; hybridization rates for 3283 (SEQ ID NO:6) and 3291 (SEQ ID NO:5) are similar for both the hairpin and single stranded targets. In contrast, 3292 (SEQ ID NO:4) which targets some stem and some loop, hybridizes $10^7$-fold more slowly to the hairpin than to the short single stranded target. Dissociation rates, on the other hand, are similar for both the hairpin and short single stranded targets.

Due to the low affinity of 3292 (SEQ ID NO:4) for the 47-mer target, a large concentration of unlabeled target was required to capture dissociated antisense oligonucleotide. Therefore, this dissociation rate was determined using unlabeled 10-mer target rather than unlabeled 47-mer target to capture dissociated antisense oligonucleotide. To confirm that use of unlabeled 10-mer target did not affect the measured dissociation rate, dissociation rates for 3291 (SEQ ID NO:5) and 3283 (SEQ ID NO:6) from 47-mer target were measured using both unlabeled 47-mer and unlabeled 10-mer as capture RNA's. Dissociation rates were unaffected by the length of the unlabeled capture RNA.

SEQUENCE LISTING ( 1 ) GENERAL INFORMATION:

( i i i ) NUMBER OF SEQUENCES: 7

( 2 ) INFORMATION FOR SEQ ID NO: 1:

( i ) SEQUENCE CHARACTERISTICS:
        ( A ) LENGTH: 47
        ( B ) TYPE: nucleic acid
        ( C ) STRANDEDNESS: single
        ( D ) TOPOLOGY: linear ( i v ) ANTI-SENSE: YES ( x i ) SEQUENCE DESCRIPTION: SEQ ID NO: 1:

GGUGGUGGUG GGCGCCGUCG GUGUGGGCAA GAGUGCGCUG ACCAUCC    47

( 2 ) INFORMATION FOR SEQ ID NO: 2:

( i ) SEQUENCE CHARACTERISTICS:
        ( A ) LENGTH: 10
        ( B ) TYPE: nucleic acid
        ( C ) STRANDEDNESS: single
        ( D ) TOPOLOGY: linear ( i v ) ANTI-SENSE: YES ( x i ) SEQUENCE DESCRIPTION: SEQ ID NO: 2:

CACCACCACC    10

( 2 ) INFORMATION FOR SEQ ID NO: 3:

( i ) SEQUENCE CHARACTERISTICS:
        ( A ) LENGTH: 10
        ( B ) TYPE: nucleic acid
        ( C ) STRANDEDNESS: single
        ( D ) TOPOLOGY: linear ( i v ) ANTI-SENSE: YES ( x i ) SEQUENCE DESCRIPTION: SEQ ID NO: 3:

GCGCCCACCA    10

( 2 ) INFORMATION FOR SEQ ID NO: 4:

( i ) SEQUENCE CHARACTERISTICS:
        ( A ) LENGTH: 10

( B ) TYPE: nucleic acid
            ( C ) STRANDEDNESS: single
            ( D ) TOPOLOGY: linear ( i v ) ANTI-SENSE: YES ( x i ) SEQUENCE DESCRIPTION: SEQ ID NO: 4:

C G A C G G C G C C                                                             1 0

( 2 ) INFORMATION FOR SEQ ID NO: 5:

( i ) SEQUENCE CHARACTERISTICS:
            ( A ) LENGTH: 10
            ( B ) TYPE: nucleic acid
            ( C ) STRANDEDNESS: single
            ( D ) TOPOLOGY: linear ( i v ) ANTI-SENSE: YES ( x i ) SEQUENCE DESCRIPTION: SEQ ID NO: 5:

C A C A C C G A C G                                                             1 0

( 2 ) INFORMATION FOR SEQ ID NO: 6:

( i ) SEQUENCE CHARACTERISTICS:
            ( A ) LENGTH: 10
            ( B ) TYPE: nucleic acid
            ( C ) STRANDEDNESS: single
            ( D ) TOPOLOGY: linear ( i v ) ANTI-SENSE: YES ( x i ) SEQUENCE DESCRIPTION: SEQ ID NO: 6:

U U G C C C A C A C                                                             1 0

( 2 ) INFORMATION FOR SEQ ID NO: 7:

( i ) SEQUENCE CHARACTERISTICS:
            ( A ) LENGTH: 10
            ( B ) TYPE: nucleic acid
            ( C ) STRANDEDNESS: single
            ( D ) TOPOLOGY: linear ( i v ) ANTI-SENSE: NO ( x i ) SEQUENCE DESCRIPTION: SEQ ID NO: 7:

C A C U C U U G C C                                                             1 0

What is claimed is:

1. A method of preparing antisense oligonucleotides targeted to a hairpin structure comprising:
   a) selecting a region predicted to have a hairpin structure corresponding to residues +18 to +64 of the coding sequence of activated H-ras mRNA;
   b) synthesizing oligonucleotides 6 to 30 nucleotides in length, said oligonucleotides being targeted to said selected region;
   c) comparing the affinities of the synthesized oligonucleotides for said selected region to the affinity of the synthesized oligonucleotides for an oligonucleotide complement having an equivalent number of nucleotides; and
   d) selecting a synthesized oligonucleotide having an affinity for said selected region which is not less than one thousandth of its affinity for the oligonucleotide complement having an equivalent number of nucleotides.

2. The method of claim 1 wherein said affinity is determined by measurement of a dissociation constant.

3. An antisense oligonucleotide comprising 10 to 30 nucleotides which is targeted to a hairpin structure corresponding to residues +18 to +64 of the coding sequence of activated H-ras mRNA.

4. An oligonucleotide of claim 3 having SEQ ID NO:2, SEQ ID NO:3, SEQ ID NO:4, SEQ ID NO: 5, SEQ ID NO:6, or SEQ ID NO:7.

5. An oligonucleotide having SEQ ID NO:5 or SEQ ID NO:6.

* * * * *